United States Patent
Deno et al.

(10) Patent No.: US 11,457,826 B2
(45) Date of Patent: Oct. 4, 2022

(54) INFORMATION PROCESSING APPARATUS, INFORMATION PROCESSING METHOD, AND NON-TRANSITORY COMPUTER-READABLE STORAGE MEDIUM

(71) Applicant: OMRON HEALTHCARE CO., LTD., Muko (JP)

(72) Inventors: Toru Deno, Kyoto (JP); Naoki Tsuchiya, Tokyo (JP); Hiroshi Usui, Kyoto (JP); Kosuke Inoue, Kyoto (JP); Yoshiyuki Morita, Nagaokakyo (JP); Yasushi Matsuoka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 294 days.

(21) Appl. No.: 16/910,610

(22) Filed: Jun. 24, 2020

(65) Prior Publication Data

US 2020/0315463 A1    Oct. 8, 2020

Related U.S. Application Data

(63) Continuation of application No. PCT/JP2018/046238, filed on Dec. 17, 2018.

(30) Foreign Application Priority Data

Dec. 27, 2017  (JP) .............................. JP2017-252651

(51) Int. Cl.
  *A61B 5/022*  (2006.01)
  *A61B 5/021*  (2006.01)
  *A61B 5/00*  (2006.01)

(52) U.S. Cl.
  CPC .......... *A61B 5/022* (2013.01); *A61B 5/02141* (2013.01); *A61B 5/681* (2013.01); *A61B 5/742* (2013.01)

(58) Field of Classification Search
  CPC ..... A61B 5/022; A61B 5/02141; A61B 5/681; A61B 5/742; A61B 5/0004;
  (Continued)

(56) References Cited

U.S. PATENT DOCUMENTS

| 2010/0286539 | A1  | 11/2010 | Ito et al. |
| 2018/0042486 | A1* | 2/2018  | Yoshizawa ........... A61B 5/0077 |
| 2022/0151784 | A1* | 5/2022  | Eigler .................... A61F 2/2487 |

FOREIGN PATENT DOCUMENTS

| JP | 2006-170751 A | 6/2006 |
| JP | 2015-228971 A | 12/2015 |

(Continued)

OTHER PUBLICATIONS

Jul. 2, 2020 International Preliminary Report on Patentability issued in International Patent Application No. PCT/JP2018/046238.
(Continued)

*Primary Examiner* — Omeed Alizada
(74) *Attorney, Agent, or Firm* — Oliff PLC

(57) ABSTRACT

According to a first aspect of the invention, an information processing apparatus includes an information acquisition unit configured to acquire first blood pressure information and second blood pressure information that is information earlier than the first blood pressure information, a blood pressure fluctuation detector configured to detect a blood pressure fluctuation exceeding a first reference value from the first and second blood pressure information, and a fluctuation information output unit configured to output blood pressure fluctuation information that reports the blood pressure fluctuation.

9 Claims, 6 Drawing Sheets

(58) Field of Classification Search
CPC .......... A61B 2562/0219; A61B 5/0235; A61B 5/7275; A61B 2560/0252; A61B 2560/0257; A61B 2560/0261; A61B 2562/0247; A61B 2562/0271; A61B 2562/029; A61B 5/02225; A61B 5/02233; A61B 5/1118; A61B 5/6824; A61B 5/6831

See application file for complete search history.

(56) References Cited

FOREIGN PATENT DOCUMENTS

| | | |
|---|---|---|
| JP | 2017-023546 A | 2/2017 |
| WO | 2009/093516 A1 | 7/2009 |
| WO | 2016/158624 A1 | 10/2016 |
| WO | 2016/185931 A1 | 11/2016 |
| WO | 2017/033608 A1 | 3/2017 |
| WO | 2018/021180 A1 | 2/2018 |

OTHER PUBLICATIONS

Mar. 5, 2019 International Search Report issued in International Patent Application No. PCT/JP2018/046238.

\* cited by examiner

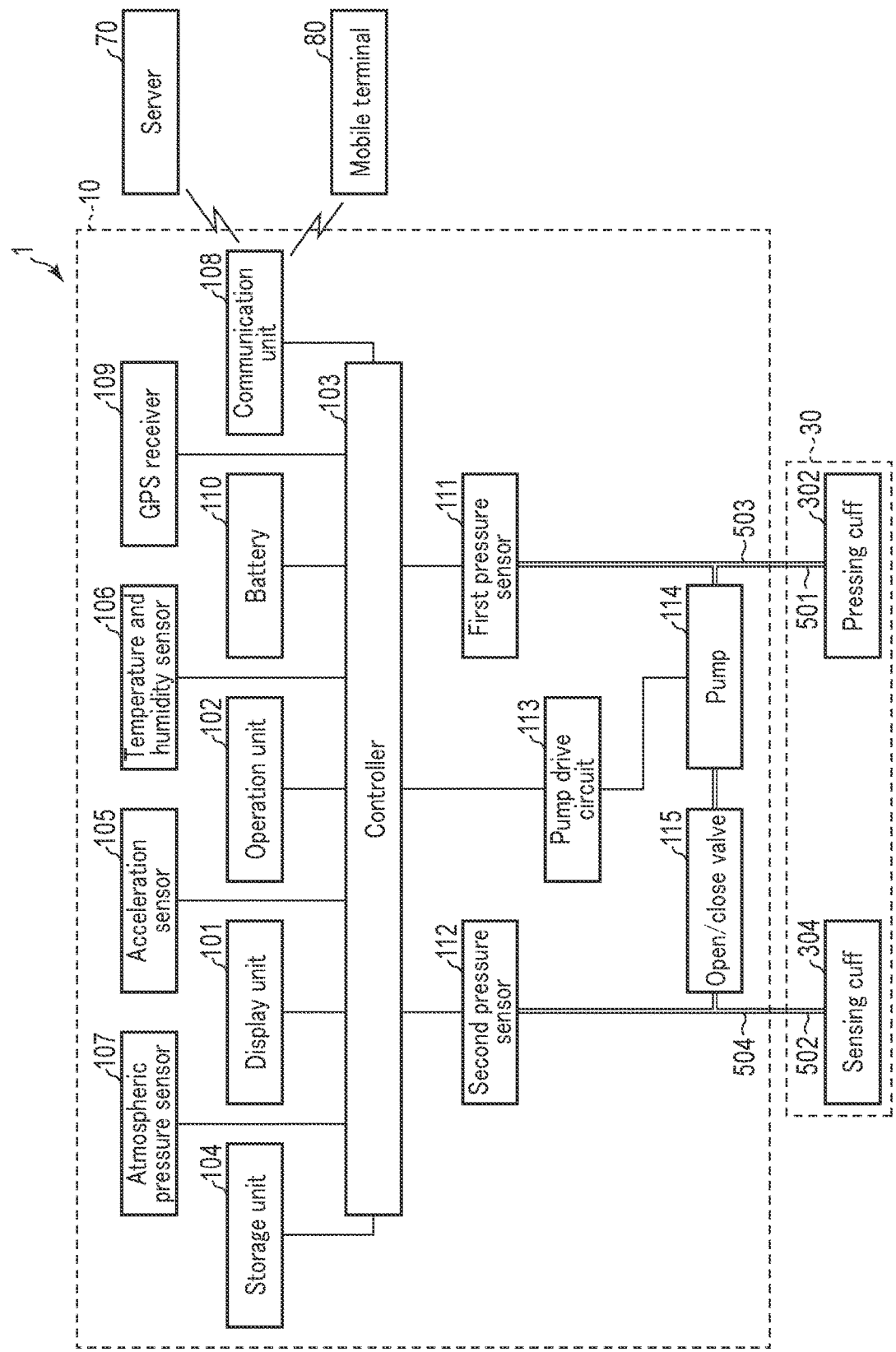
F I G. 2

INFORMATION PROCESSING APPARATUS, INFORMATION PROCESSING METHOD, AND NON-TRANSITORY COMPUTER-READABLE STORAGE MEDIUM

CROSS-REFERENCE TO RELATED APPLICATIONS

This application is a Continuation Application of PCT Application No. PCT/JP2018/046238, filed Dec. 17, 2018 and based upon and claiming the benefit of priority from Japanese Patent Application No. 2017-252651, filed Dec. 27, 2017, the entire contents of all of which are incorporated herein by reference.

FIELD

The present invention relates generally to an information processing apparatus, an information processing method, and a non-transitory computer-readable storage medium.

BACKGROUND

In recent years, a wearable blood pressure monitor capable of easily measuring blood pressure regardless of place has been developed. Jpn. Pat. Appln. KOKAI Publication No. 2017-023546 discloses, as an example thereof, a wearable blood pressure monitor that starts blood pressure measurement in response to an input operation of a measurement instruction.

Such a wearable blood pressure monitor can easily measure blood pressure in various situations. For example, blood pressure values can be measured and recorded at various locations, such as at home or at work, and blood pressure values can be measured and recorded at various times, including times away from home. Blood pressure values measured in these various situations are used for health management and the like.

SUMMARY

By using the wearable blood pressure monitor as described above, blood pressure measurement may be performed easily in various situations such as at home or at work. However, blood pressure fluctuations that can occur in daily life are often not noticed. For example, it is known that an environmental change such as a rapid temperature change may cause blood pressure fluctuations that should be noted in health management. In order to notice such blood pressure fluctuations, it is necessary to perform operations such as measuring the blood pressure on a daily basis and comparing a past measurement value with a current measurement value.

In one aspect, the present invention is made in view of the above circumstances, and the object thereof is to provide a technique that provides a measurement subject or the like with an opportunity to recognize the blood pressure fluctuation.

In order to solve the above-described problems, the present invention adopts the following configurations.

According to a first aspect of the invention, an information processing apparatus comprises an information acquisition unit configured to acquire first blood pressure information and second blood pressure information that is information earlier than the first blood pressure information, a blood pressure fluctuation detector configured to detect a blood pressure fluctuation exceeding a first reference value from the first and second blood pressure information, and a fluctuation information output unit configured to output blood pressure fluctuation information that reports the blood pressure fluctuation.

According to the above configuration, by outputting the blood pressure fluctuation information based on the detection of the blood pressure fluctuation, it is possible to provide an opportunity to recognize the blood pressure fluctuation by notifying the measurement subject of the blood pressure fluctuation. For example, a blood pressure fluctuation exceeding the first reference value imposes a burden on the blood vessel; however, since the measurement subject or the like can become aware of the occurrence of blood pressure fluctuation, the measurement subject can discuss improving the living environment or the like.

According to a second aspect of the invention, the information processing apparatus according to the first aspect further comprises an environmental change detector configured to detect an environmental change exceeding a second reference value from first environmental information and the second environmental information that is information earlier than the first environmental information, a blood pressure measurement unit configured to measure the first blood pressure information based on detection of the environmental change, and a blood pressure information output unit configured to output the first blood pressure information.

According to the above configuration, the blood pressure fluctuation may occur based on the environmental change exceeding the second reference value, and the detection probability of the blood pressure fluctuation can be increased.

According to a third aspect of the invention, in the information processing apparatus according to the second aspect, the blood pressure measurement unit measures the second blood pressure information based on one of a measurement instruction corresponding to an input operation or a measurement instruction corresponding to a measurement schedule, and the blood pressure information output unit outputs the second blood pressure information.

According to the above configuration, it is possible to measure the second blood pressure information at a timing according to the intention of the measurement subject or the like based on the measurement instruction corresponding to the input operation. Alternatively, the second blood pressure information can be measured at a timing determined by the measurement schedule.

According to a fourth aspect of the invention, in the information processing apparatus according to the third aspect, the blood pressure fluctuation detector updates the second blood pressure information in accordance with acquisition of blood pressure information.

According to the above configuration, it is possible to detect the blood pressure fluctuation from the first blood pressure information and the second blood pressure information updated in accordance with the acquisition of the blood pressure information.

According to a fifth aspect of the invention, in the information processing apparatus according to any one of the second to fourth aspects, the environmental change detector updates the second environmental information in accordance with acquisition of environmental information.

According to the above configuration, it is possible to detect an environmental change from the first environmental information and the second environmental information updated in accordance with the acquisition of the environmental information.

According to a sixth aspect of the invention, in the information processing apparatus according to any one of the second to fifth aspects, the environmental change detector detects the environmental change exceeding the second reference value from first temperature information corresponding to the first environmental information and second temperature information corresponding to the second environmental information.

According to the above configuration, it is possible to measure the first blood pressure information using a temperature change exceeding the second reference value as a trigger, and thus it is possible to increase the detection probability of the blood pressure fluctuation.

According to a seventh aspect of the invention, in the information processing apparatus according to any one of the second to sixth aspects, the fluctuation information output unit outputs the blood pressure fluctuation information including information indicating the environmental change.

According to the above configuration, by outputting the blood pressure fluctuation information, it is possible to notify the measurement subject or the like of the environmental change in addition to the blood pressure fluctuation. For example, the measurement subject or the like can become aware of the blood pressure fluctuation according to the environmental change, and can discuss improving the living environment or the like.

According to an eighth aspect of the invention, in the information processing apparatus according to any one of the second to seventh aspects, the blood pressure information output unit outputs the first and second blood pressure information in association with information indicating a blood pressure measurement situation of a measurement subject, and the fluctuation information output unit outputs the blood pressure fluctuation information including information indicating the blood pressure measurement situation.

According to the above configuration, by outputting the blood pressure fluctuation information, it is possible to notify the measurement subject or the like of the blood pressure measurement situation in addition to the blood pressure fluctuation. For example, the measurement subject or the like can become aware of the blood pressure measurement situation when the blood pressure fluctuation has occurred, and can discuss measures to be taken against the blood pressure fluctuation or the like from the blood pressure measurement situation.

According to a ninth aspect of the invention, in the information processing apparatus according to the eighth aspect, the information indicating the blood pressure measurement situation includes a blood pressure measurement position of the measurement subject.

According to the above configuration, by outputting the blood pressure fluctuation information, it is possible to notify the measurement subject or the like of the blood pressure measurement position in addition to the blood pressure fluctuation. For example, the measurement subject or the like can become aware of the blood pressure measurement position of the time the blood pressure fluctuation has occurred, and can discuss measures to be taken against the blood pressure fluctuation from the blood pressure measurement position.

According to a tenth aspect of the invention, in the information processing apparatus according to the sixth aspect, the environmental change detector detects the environmental change in a case where at least one of the first or second temperature information is below a temperature reference value.

According to the above configuration, in a case where at least one of the first or the second temperature information is below the temperature reference value, the environmental change is detected, and the blood pressure is measured to detect the blood pressure fluctuation in the environmental change at a low temperature below the temperature reference value. By excluding a part of the temperature environment in which the blood pressure fluctuation occurrence probability is considered to be low from the target of the blood pressure measurement, it is possible to relieve the measurement subject of the burden of blood pressure measurement and to improve comfortableness. In addition, the amount of blood pressure information to be recorded can be reduced, thereby reducing the amount of storage resources used.

According to an eleventh aspect of the invention, an information processing method performed by an information processing apparatus comprises acquiring first blood pressure information and second blood pressure information that is information earlier than the first blood pressure information, detecting a blood pressure fluctuation exceeding a first reference value from the first and second blood pressure information, and outputting blood pressure fluctuation information reporting the blood pressure fluctuation.

According to the above configuration, it is possible to obtain the same effect as the first aspect described above.

According to the above configuration, it is possible to obtain the same effect as that of any one of the first to tenth aspects.

According to the present invention, it is possible to provide a technique for providing a measurement subject or the like with an opportunity to recognize blood pressure fluctuation.

BRIEF DESCRIPTION OF THE DRAWINGS

FIG. 2 is a block diagram showing an example of a blood pressure monitor according to an embodiment.

DETAILED DESCRIPTION

Hereinafter, an embodiment according to an aspect of the present invention (hereinafter, also referred to as "present embodiment") will be described with reference to the drawings. However, the embodiment described below is merely an example of the present invention in all respects. As a matter of course, various alterations and modifications can be made, without departing from the scope of the invention. That is, in carrying out the present invention, a specific configuration according to the embodiment may be adopted as appropriate. Note that signals and the like mentioned in the present embodiment are described in a natural language, but more specifically, they are designated in a pseudo language, a command, a parameter, a machine language, or the like recognizable by a computer.

Embodiment (Configuration)

Figure 1:
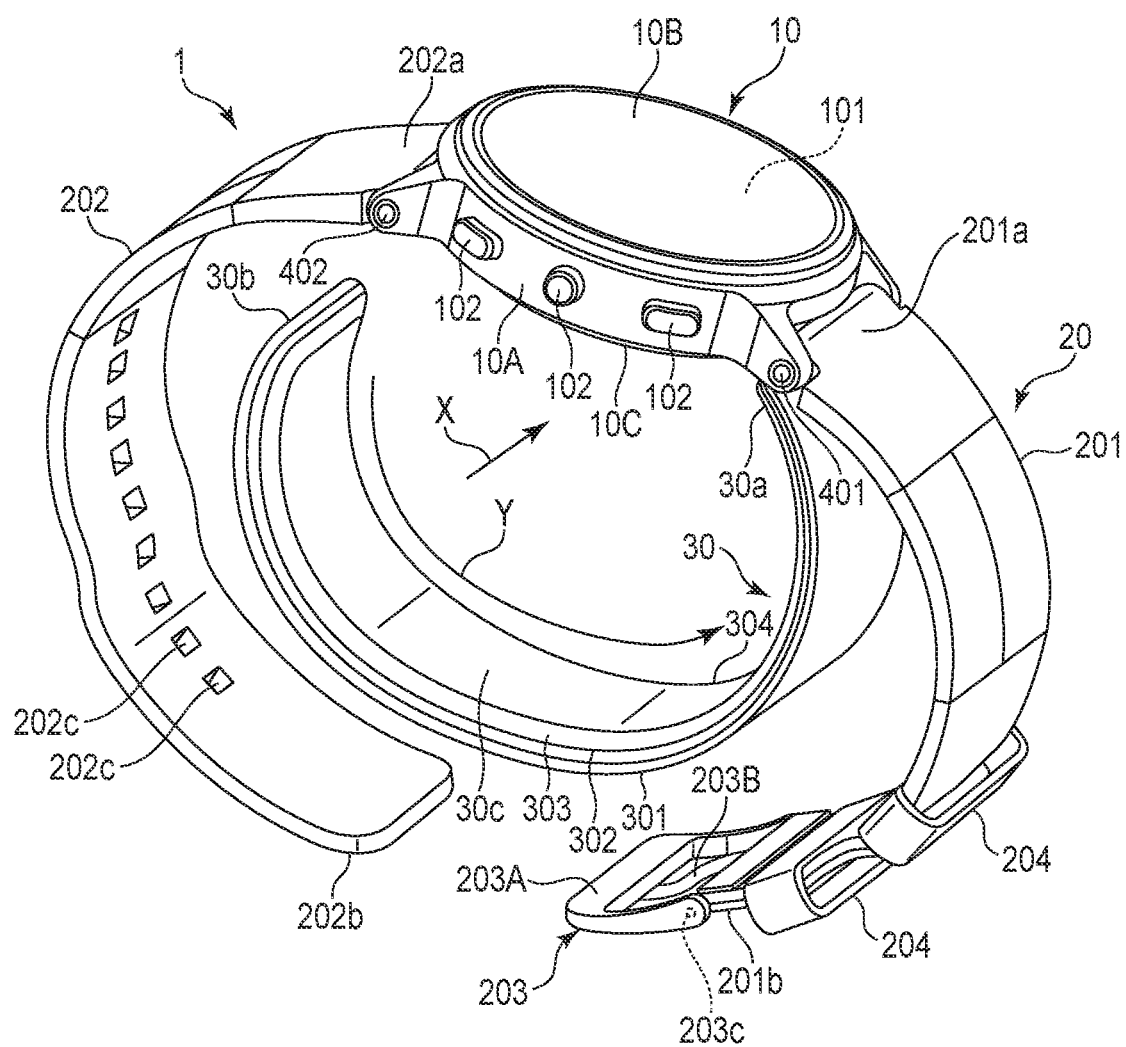
FIG. 1 is an external view showing an example of a blood pressure monitor according to an embodiment.

FIG. 1 shows an appearance of a blood pressure monitor 1 as an embodiment of an information processing apparatus according to the present invention.

The blood pressure monitor 1 is a wristwatch-type wearable device. The blood pressure monitor 1 has a blood pressure measurement function as a blood pressure measurement unit, and further has various information processing functions. The information processing functions include, for example, an activity amount measurement function, a step count measurement function, a sleep state measurement function, and an environment (temperature, humidity, and atmospheric pressure) measurement function. The blood pressure monitor 1 is, for example, a blood pressure monitor of a type that starts blood pressure measurement based on an input of a blood pressure measurement start instruction by a measurement subject or a trigger signal autonomously generated by the blood pressure monitor 1.

The blood pressure monitor 1 includes a main body 10, a belt 20, and a cuff structure 30.

The configuration of the main body 10 will be described.

The main body 10 is configured to be able to mount a plurality of elements such as elements of a control system of the blood pressure monitor 1.

The main body 10 includes a case 10A, a glass 10B, and a back cover 10C.

The case 10A has, for example, a substantially short cylindrical shape. The case 10A is provided with a pair of projecting lugs for attaching the belt 20 at each of the two positions on its side surface.

The glass 10B is attached to an upper portion of the case 10A. The glass 10B has, for example, a circular shape.

The back cover 10C is detachably attached to the lower portion of the case 10A so as to face the glass 10B.

The main body 10 includes a display unit 101 and an operation unit 102.

The display unit 101 displays various kinds of information. The display unit 101 is provided in the main body 10 at a position that can be visually recognized by the measurement subject through the glass 10B. The display unit 101 is, for example, a liquid crystal display (LCD) The display unit 101 may be an organic electro luminescence (EL) display. The display unit 101 may have a function of displaying various kinds of information, and is not limited thereto. The display unit 101 may include a light emitting diode (LED).

The operation unit 102 is an element for inputting various instructions to the blood pressure monitor 1. The operation portion 102 is provided on a side surface of the main body 10. The operation unit 102 includes, for example, one or more push switches. The operation unit 102 may be a pressure-sensitive (resistive) or proximity (capacitive) touch panel switch. The operation unit 102 may have a function of inputting various instructions to the blood pressure monitor 1, and is not limited thereto.

Examples of switches included in the operation unit 102 will be described.

The operation unit 102 includes a measurement switch for instructing a starting or stopping of blood pressure measurement. The operation unit 102 may include a home switch for returning the display screen of the display unit 101 to a predetermined home screen, and a record call switch for causing the display unit 101 to display a measurement record of the past blood pressure, activity amount, and the like.

The main body 10 includes a plurality of elements other than the display unit 101 and the operation unit 102. A plurality of elements mounted on the main body 10 will be described later.

The configuration of the belt 20 will be described.

The belt 20 is configured to be able to surround a measurement site (for example, a left wrist) of the measurement subject. The width direction of the belt 20 is defined as an X direction. The direction in which the belt 20 surrounds the measurement site is a Y direction.

The belt 20 includes a first belt portion 201, a second belt portion 202, a buckle 203, and a belt holding portion 204.

The first belt portion 201 has a band shape extending from the main body 10 to one side in one direction (right side in FIG. 1). A root portion 201a of the first belt portion 201 close to the main body 10 is rotatably attached to a pair of lugs of the main body 10 via a connecting rod 401.

The second belt portion 202 has a band shape extending from the main body 10 to the other side in one direction (left side in FIG. 1). A root portion 202a of the second belt portion 202 close to the main body 10 is rotatably attached to a pair of lugs of the main body 10 via a connecting rod 402. A plurality of small holes 202c are formed between the root portion 202a and a distal end portion 202b of the second belt portion 202 remote from the main body 10 so as to penetrate the second belt portion 202 in the thickness direction.

The buckle 203 is configured to be able to fasten the first belt portion 201 and the second belt portion 202. The buckle 203 is attached to a distal end portion 201b of the first belt portion 201 that is far from the main body 10. The buckle 203 includes a frame-shaped body 203A, a fastening rod 203B, and a connecting rod 203C.

The frame-shaped body 203A and the fastening rod 203B are rotatably attached to the distal end portion 201b of the first belt portion 201 via the connecting rod 203C. The frame-shaped body 203A and the fastening rod 203B are made of, for example, a metal material. The frame-shaped body 203A and the fastening rod 203B may be made of a plastic material. When the first belt portion 201 and the second belt portion 202 are fastened, the distal end portion 202b of the second belt portion 202 is passed through the frame-shaped body 203A. The fastening rod 203B is inserted into one of the plurality of small holes 202c of the second belt portion 202.

The belt holding portion 204 is attached between the root portion 201a and the distal end portion 201b of the first belt portion 201. When the first belt portion 201 and the second belt portion 202 are fastened, the distal end portion 202b of the second belt portion 202 is passed through the belt holding portion 204.

The configuration of the cuff structure 30 will be described.

The cuff structure 30 is configured to be able to press a measurement site during blood pressure measurement.

The cuff structure 30 has a band shape extending along the Y direction. The cuff structure 30 faces the inner peripheral surface of the belt 20. One end 30a of the cuff structure 30 is attached to the main body 10. The other end 30b of the cuff structure 30 is a free end. Therefore, the cuff structure 30 can be separated from the inner peripheral surface of the belt 20.

The cuff structure 30 includes a curler 301, a pressing cuff 302, a back plate 303, and a sensing cuff 304.

The curler 301 is disposed at the outermost periphery of the cuff structure 30. The curler 301 is curved along the Y direction in a natural state. The curler 301 is a resin plate having a predetermined flexibility and hardness. The resin plate is made of, for example, polypropylene.

The pressing cuff 302 is disposed along the inner peripheral surface of the curler 301. The pressing cuff 302 has a bag shape. A flexible tube 501 (shown in FIG. 2) is attached to the pressing cuff 302. The flexible tube 501 is an element for supplying a pressure transmission fluid (hereinafter also simply referred to as "fluid") from the main body 10 side or discharging the fluid from the pressing cuff 302. The fluid is, for example, air. When the fluid is supplied to the pressing cuff 302, the pressing cuff 302 is inflated and compresses the measurement site.

The pressing cuff 302 may include, for example, two fluid bags stacked in the thickness direction. Each fluid bag is formed of, for example, a stretchable polyurethane sheet. As fluid is supplied to the pressing cuff 302, fluid flows into each fluid bag. As each fluid bag inflates, the pressing cuff 302 inflates. The back plate 303 is disposed along the inner peripheral surface of the pressing cuff 302.

The back plate 303 has a band shape. The back plate 303 is made of resin, for example. The resin is, for example, polypropylene. The back plate 303 functions as a reinforcing plate. Therefore, the back plate 303 can transmit the pressing force from the pressing cuff 302 to the entire region of the sensing cuff 304.

On the inner peripheral surface and the outer peripheral surface of the back plate 303, a plurality of grooves having a V-shaped or U-shaped cross section extending in the direction X are provided in parallel to be spaced apart from each other in the direction Y. Because the back plate 303 is flexible, the back plate 303 does not prevent the cuff structure 30 from bending.

The sensing cuff 304 is disposed along the inner peripheral surface of the back plate 303. The sensing cuff 304 has a bag shape. The sensing cuff 304 includes a first sheet 304A (shown in FIG. 3) and a second sheet 304B (shown in FIG. 3) facing the first sheet 304A. The first sheet 304A corresponds to an inner peripheral surface 30c of the cuff structure 30. Therefore, the first sheet 304A contacts the measurement site. The second sheet 304B faces the inner peripheral surface of the back plate 303. The first sheet 304A and the second sheet 304B are, for example, stretchable polyurethane sheets. A flexible tube 502 (shown in FIG. 2) is attached to a sensing cuff 304. The flexible tube 502 is an element for supplying fluid to the sensing cuff 304 or discharging fluid from the sensing cuff 304.

A plurality of elements mounted on the main body 10 will now be described.

FIG. 2 is a block diagram showing a hardware configuration of the blood pressure monitor 1.

In addition to the display unit 101 and the operation unit 102, the main body 10 includes a controller 103, a storage unit 104, an acceleration sensor 105, a temperature and humidity sensor 106, an atmospheric pressure sensor 107, a communication unit 108, a GPS (global positioning system) receiver 109, a battery 110, a first pressure sensor 111, a second pressure sensor 112, a pump drive circuit 113, a pump 114, and an open/close valve 115.

The controller 103 includes a processor constituting a computer, a random access memory (RAM), a read only memory (ROM), and the like, and controls each component according to information processing based on a program (information processing program) stored in at least one of the ROM or the storage unit 104. For example, the processor is a central processing unit (CPU). The program is a command for operating the controller 103.

The controller 103 also stores data acquired from the acceleration sensor 105, the temperature and humidity sensor 106, the atmospheric pressure sensor 107, the communication unit 108, the GPS receiver 109, the first pressure sensor 111, and the second pressure sensor 112 in the storage unit 104. The configuration of each unit implemented by the controller 103 will be described later.

The storage unit 104 is, for example, an auxiliary storage device such as a hard disk drive or a solid state drive. For example, the storage unit 104 stores a program executed by the controller 103. The storage unit 104 also stores control data used for controlling the blood pressure monitor 1, setting data for setting various functions of the blood pressure monitor 1, and the like. The storage unit 104 is also used as a work memory and the like when the program is executed.

The storage unit 104 also stores blood pressure-related information. For example, the blood pressure related information includes a plurality of pieces of blood pressure information measured at different dates and times, and a situation of the measurement subject when the blood pressure associated with each piece of blood pressure information was measured (hereinafter also referred to as "blood pressure measurement situation"). For example, the blood pressure information includes blood pressure values (systolic blood pressure (SBP), diastolic blood pressure (DBP), and the like). The blood pressure measurement situation includes time information (measurement date and time) acquired according to the timing of blood pressure measurement, and also includes at least one of position information (measurement position), acceleration information, temperature and humidity information, atmospheric pressure information, action schedule information, or the like. For example, the above-described timing of the blood pressure measurement is one of timing at the start of the blood pressure measurement, timing during the blood pressure measurement, or timing at the end of the blood pressure measurement. Furthermore, the acceleration information may be information acquired at a timing that is a predetermined time (for example, one minute or five minutes) before the start of the blood pressure measurement.

The acceleration sensor 105 is a three-axis acceleration sensor. The acceleration sensor 105 outputs acceleration information indicating accelerations in three directions orthogonal to each other to the controller 103. The acceleration information is an example of information indicating the movement of the measurement subject. Using the acceleration information, the controller 103 can calculate the amount of activity of the measurement subject in various activities such as housework and desk work as well as walking. The activity amount is, for example, an index related to the activity of the measurement subject such as a moving (walking) distance, calorie consumption, or a fat burning amount. The controller 103 can also use the acceleration information to estimate whether the measurement subject is in a state of before sleeping, sleeping, or after waking. The controller 103 can also estimate whether or not the measurement subject is exercising using the acceleration information.

The temperature and humidity sensor 106 measures the environmental temperature (room temperature) and humidity around the blood pressure monitor 1. The temperature and humidity sensor 106 outputs environmental information indicating the environmental temperature and humidity to the controller 103. For example, an environmental change (temperature change) such as a temperature is considered one of the elements that can cause a blood pressure fluctuation in a human. Therefore, the environmental temperature is information that can be a factor in blood pressure fluctuation of the measurement subject.

The atmospheric pressure sensor 107 detects the atmospheric pressure around the blood pressure monitor 1. The atmospheric pressure sensor 107 outputs environmental information indicating the atmospheric pressure to the controller 103. The controller 103 can measure the number of steps, the number of fast walking steps, the number of stair-climbing steps, and the like of the measurement subject using the environmental information and the acceleration information indicating the atmospheric pressure. For example, an environmental change (atmospheric pressure change) of the atmospheric pressure, etc. is considered one of the elements that can cause a blood pressure fluctuation in a human. Therefore, the atmospheric pressure is information that can be a factor in blood pressure fluctuation of the measurement subject.

The communication unit 108 is an interface for connecting the blood pressure monitor 1 to at least one of a server 70 or a mobile terminal 80. The mobile terminal 80 is, for example, a smartphone or a tablet terminal. It is assumed that the mobile terminal 80 is owned by the measurement subject. The communication unit 108 is controlled by the controller 103. The communication unit 108 transmits information to at least one of the server 70 or the mobile terminal 80 via a network. The communication unit 108 transfers information received from at least one of the server 70 or the mobile terminal 80 via the network to the controller 103. The communication via the network may be either wireless or wired. The network is, for example, the Internet, but is not limited thereto. The network may be another type of network such as a hospital local area network (LAN), or may be a one-to-one communication using a USB cable or the like. The communication unit 108 may include a micro USB connector. The communication unit 108 may transmit information to the mobile terminal 80 by short-range wireless communication such as Bluetooth (registered trademark).

The GPS receiver 109 receives GPS signals transmitted from a plurality of GPS satellites and outputs the received GPS signals to the controller 103. The controller 103 calculates the current position of the blood pressure monitor 1, that is, the current position of the measurement subject wearing the blood pressure monitor 1, by performing distance measurement calculation based on the GPS signals. The blood pressure monitor 1 does not necessarily have to include the distance measurement calculation function by the GPS receiver 109 and the controller 103. In this case, the blood pressure monitor 1 acquires position information indicating the current position calculated by the mobile terminal 80 from the mobile terminal 80 via the communication unit 108. The position information calculated by the mobile terminal 80 corresponds to the current position of the blood pressure monitor 1. For example, the mobile terminal 80 may include a GPS reception function and calculate the position information from a GPS signal received by the GPS reception function, or the mobile terminal 80 may acquire the position information by communication with a base station.

The battery 110 is, for example, a rechargeable second battery. The battery 110 supplies power to each element mounted on the main body 10. The battery 110 supplies power to, for example, the display unit 101, the operation unit 102, the controller 103, the storage unit 104, the acceleration sensor 105, the temperature and humidity sensor 106, the atmospheric pressure sensor 107, the communication unit 108, the first pressure sensor 111, the second pressure sensor 112, the pump drive circuit 113, the pump 114, and the open/close valve 115.

The first pressure sensor 111 is, for example, a piezoresistive pressure sensor. The first pressure sensor 111 detects the pressure in the pressing cuff 302 via the flexible tube 501 and a first flow path forming member 503 constituting a first flow path. The first pressure sensor 111 outputs pressure data to the controller 103.

The second pressure sensor 112 is, for example, a piezoresistive pressure sensor. The second pressure sensor 112 detects the pressure in the sensing cuff 304 via the flexible tube 502 and a second flow path forming member 504 constituting a second flow path. The second pressure sensor 112 outputs pressure data to the controller 103.

The pump drive circuit 113 drives the pump 114 based on a control signal from the controller 103.

The pump 114 is, for example, a piezoelectric pump. The pump 114 is fluidly connected to the pressing cuff 302 via the first flow path. The pump 114 can supply fluid to the pressing cuff 302 through the first flow path. The pump 114 is equipped with an exhaust valve (not shown) whose opening and closing are controlled in accordance with ON/OFF of the pump 114. That is, the exhaust valve closes when the pump 114 is turned on to assist in enclosing air within the pressing cuff 302. On the other hand, when the pump 114 is turned off, the exhaust valve is opened to discharge the air in the pressing cuff 302 to the atmosphere through the first flow path. The exhaust valve has a function of a check valve, and the discharged air does not flow back.

The pump 114 is further fluidly connected to the sensing cuff 304 via the second flow path. The pump 114 can supply fluid to the sensing cuff 304 through the second flow path.

The open/close valve 115 is interposed in the second flow path forming member 504. The open/close valve 115 is, for example, a normally open electromagnetic valve. The opening and closing (opening degree) of the open/close valve 115 is controlled based on a control signal from the controller 103. When the open/close valve 115 is in an open state, the pump 114 can supply fluid to the sensing cuff 304 through the second flow path.

A state in which the blood pressure monitor 1 is attached to the measurement site (hereinafter, also referred to as "attached state") will be described.

Figure 3:
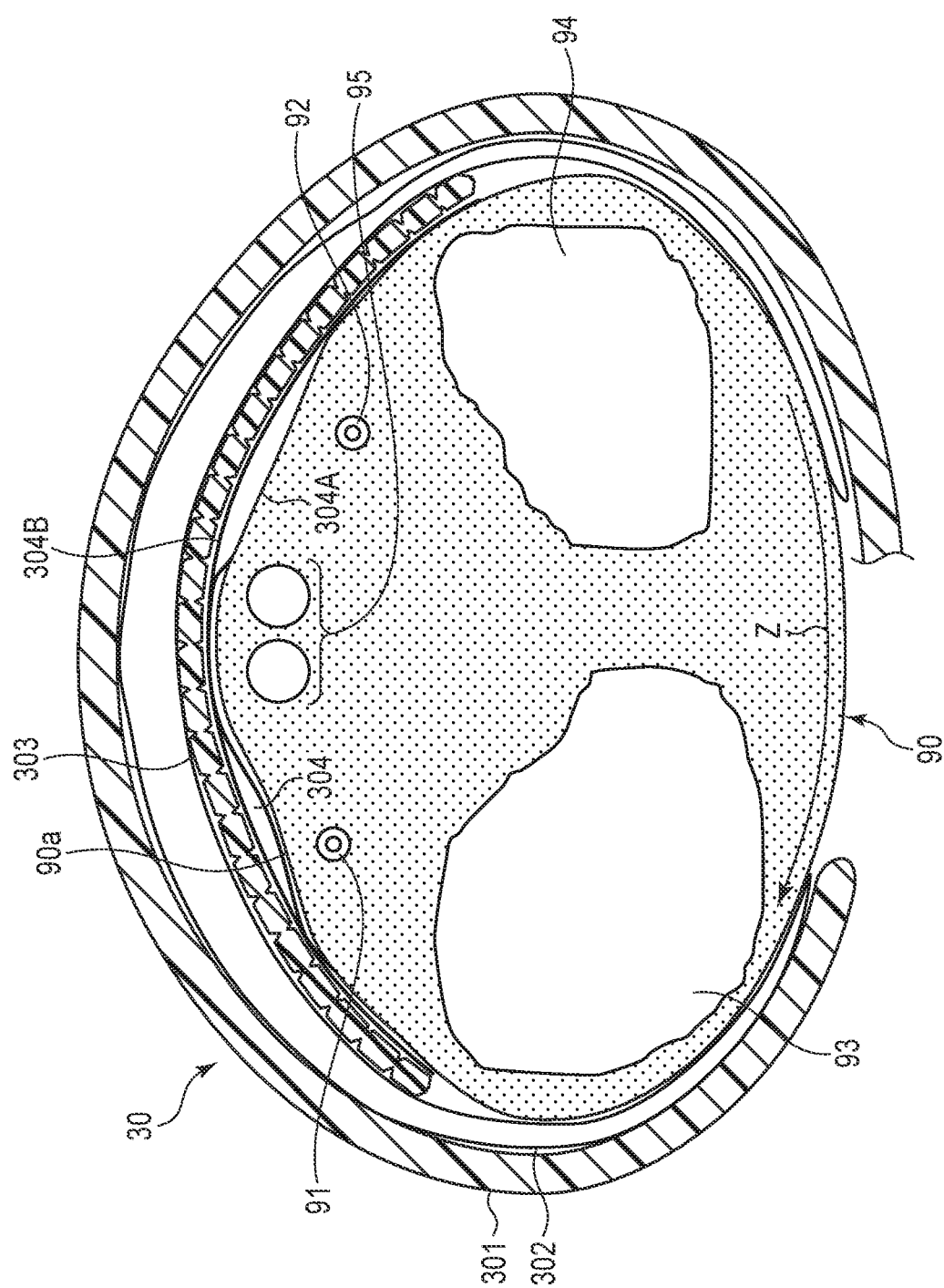
FIG. 3 is a cross-sectional view showing an example of a blood pressure monitor according to an embodiment.

FIG. 3 is a view showing a cross section perpendicular to the left wrist 90 which is the measurement site in the attached state. The main body 10 and the belt 20 are not shown. FIG. 3 shows the radial artery 91, ulnar artery 92, radius 93, ulna 94, and tendon 95 of the left wrist 90.

In this attached state, curler 301 extends along the outer periphery (Z direction) of left wrist 90. The pressing cuff 302 extends along the Z direction on the inner peripheral side of the curler 301. The back plate 303 is interposed between the pressing cuff 302 and the sensing cuff 304, and extends along the Z direction. The sensing cuff 304 is in contact with the left wrist 90 and extends in the Z direction so as to cross an artery passing portion 90a of the left wrist 90. The belt 20, the curler 301, the pressing cuff 302, and the back plate 303 function as a pressing member capable of generating a pressing force toward the left wrist 90, and press the left wrist 90 via the sensing cuff 304.

A configuration of software included in the controller 103 will now be described.

Figure 4:
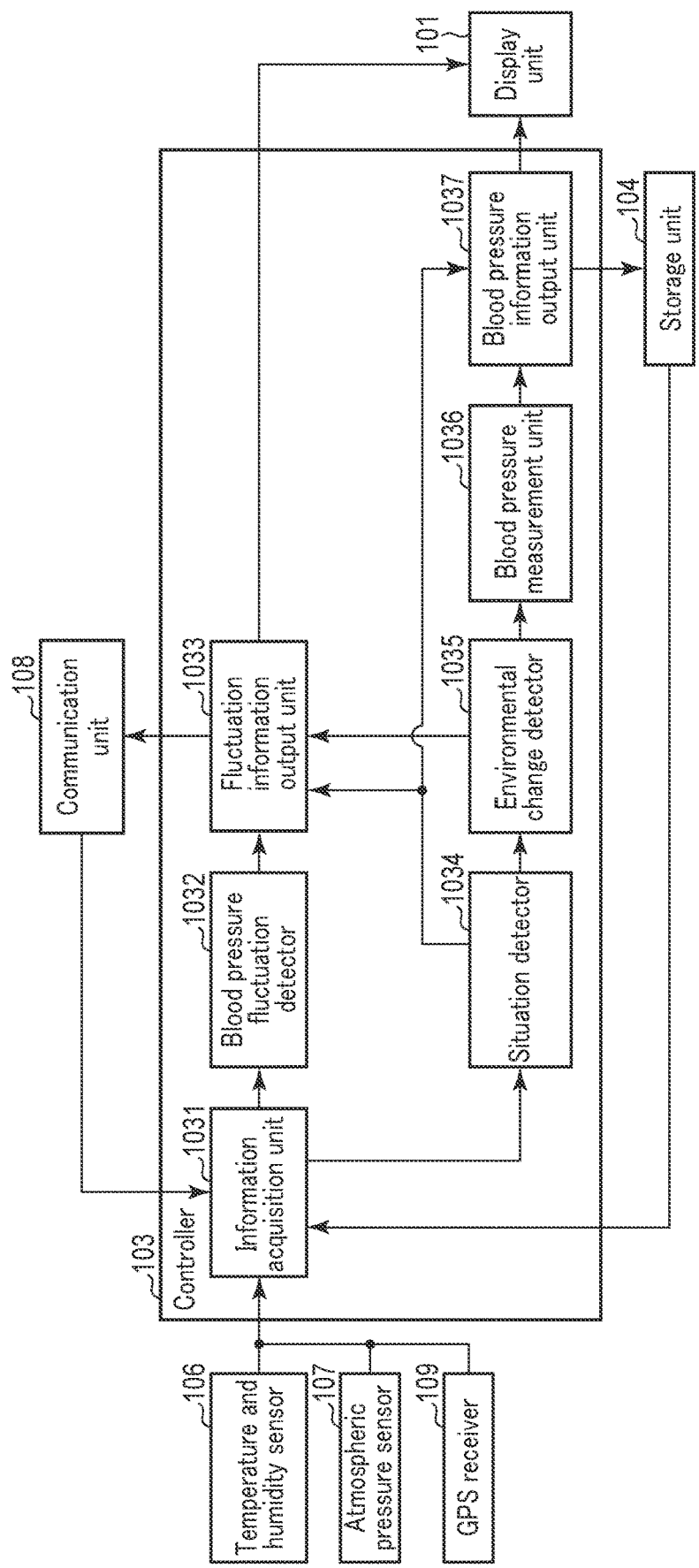
FIG. 4 is a functional block diagram showing an example of a blood pressure monitor according to an embodiment.

FIG. 4 is a block diagram showing a configuration of software included in the controller 103 of the blood pressure monitor 1. The controller 103 includes, as characteristic control functions according to the embodiment, an information acquisition unit 1031, a blood pressure fluctuation detector 1032, a fluctuation information output unit 1033, a situation detector 1034, an environmental change detector 1035, a blood pressure measurement unit 1036, and a blood pressure information output unit 1037. These control functions are realized by causing a processor to execute a program stored in a ROM or the like. Note that each control function unit may be distributed and implemented in two or more processors.

The configuration of the information acquisition unit 1031 will be described.

The information acquisition unit 1031 periodically acquires the blood pressure-related information from the storage unit 104, or monitors the storage unit 104, acquires the blood pressure-related information from the storage unit 104 in accordance with the update (additional writing) of the information stored in the storage unit 104, and outputs the sequentially acquired blood pressure-related information to the blood pressure fluctuation detector 1032. For example, the information acquisition unit 1031 acquires first blood pressure-related information (hereinafter, also referred to as "current blood pressure-related information") including a first blood pressure measurement situation (including a first blood pressure measurement date and time) and first blood pressure information (hereinafter, also referred to as "current blood pressure information") associated with the first blood pressure measurement situation, and second blood pressure-related information (hereinafter, also referred to as "past blood pressure-related information") including a second blood pressure measurement situation (including a second blood pressure measurement date and time, which is earlier than the first blood pressure measurement date and time) and second blood pressure information (hereinafter, also referred to as "past blood pressure information") associated with the second blood pressure measurement situation. The past blood pressure-related information (past blood pressure information) may be information obtained by a measurement in the past or information obtained by a plurality of measurements in the past.

Furthermore, the information acquisition unit 1031 constantly acquires environmental information and outputs the sequentially acquired environmental information to the situation detector 1034. For example, the environmental information is at least one of temperature, humidity, or atmospheric pressure around the blood pressure monitor 1. Furthermore, the information acquisition unit 1031 acquires current time information and outputs the current time information to the situation detector 1034. Furthermore, the information acquisition unit 1031 may acquire at least one piece of information among the position information, the acceleration information, the registered action schedule information, and the like, and output the at least one piece of information to the situation detector 1034.

For example, the information acquisition unit 1031 acquires time information from the communication unit 108. The communication unit 108 receives time information from the server 70 or the mobile terminal 80. In the case where the blood pressure monitor 1 has a clock function, the information acquisition unit 1031 may acquire time information provided by the clock function. In this case, the clock function may correct the current date and time based on the time information acquired from the communication unit 108 and provide the corrected time information.

For example, the information acquisition unit 1031 acquires temperature and humidity information from the temperature and humidity sensor 106 and acquires atmospheric pressure information from the atmospheric pressure sensor 107.

For example, the information acquisition unit 1031 acquires a GPS signal from the GPS receiver 109. Alternatively, the information acquisition unit 1031 may acquire position information indicating the current position from the communication unit 108.

For example, the information acquisition unit 1031 acquires the action schedule information from the communication unit 108. The communication unit 108 receives the action schedule information from the mobile terminal 80. For example, schedule management application software is installed in the mobile terminal 80, and the schedule management application software creates and registers action schedule information and outputs the action schedule information outside. For example, the action schedule information includes bedtime, wake-up time, and the like.

For example, the information acquisition unit 1031 acquires acceleration information from the acceleration sensor 105.

The configuration of the blood pressure fluctuation detector 1032 will be described.

Blood pressure fluctuation detector 1032 receives blood pressure-related information sequentially acquired by the blood pressure measurement operation of blood pressure measurement unit 1036 based on at least one of the input operation of blood pressure measurement to operation unit 102 or the blood pressure measurement schedule registered in storage unit 104, and detects a blood pressure fluctuation exceeding a blood pressure reference value (first reference value) from the first blood pressure information (current blood pressure information) at a first measurement date and time (for example, current date and time) and the second blood pressure information (past blood pressure information) at a second measurement date and time that is earlier than the first measurement date and time based on a plurality of pieces of blood pressure information included in the blood pressure-related information and the blood pressure measurement situation (including the measurement date and time) associated with each piece of blood pressure information. The blood pressure fluctuation detector 1032 sequentially updates the first and second blood pressure information according to the blood pressure-related information (including the blood pressure information) sequentially acquired according to the passage of time. The blood pressure fluctuation detector 1032 detects the blood pressure fluctuation exceeding the blood pressure reference value from the updated first blood pressure information and the updated second blood pressure information. For example, in the case where a difference between the value of the first blood pressure information at the first measurement date and time obtained by a measurement and the second blood pressure information obtained by a past measurement closest to the first measurement date and time exceeds the blood pressure reference value, the difference is detected as the blood pressure fluctuation. Alternatively, in the case where a difference between the value of the first blood pressure information at the first measurement date and time obtained by a measurement and an average value of a plurality of pieces of the second blood pressure information obtained by a plurality of measurements performed earlier than the first measurement date and time exceeds the blood pressure reference value, the difference is detected as the blood pressure fluctuation. For example, in the case where a difference between the value of the first blood pressure information and the average value of a plurality of pieces of blood pressure information in the past hour, the past six hours, the past day, or the past week exceeds the blood pressure reference value, the difference is detected as the blood pressure fluctuation. For example, by setting 10 mmHg as the blood pressure reference value, a difference exceeding 10 mmHg is detected as the blood pressure fluctuation.

The configuration of the fluctuation information output unit 1033 will be described.

The fluctuation information output unit 1033 outputs blood pressure fluctuation information for reporting the blood pressure fluctuation. For example, the blood pressure fluctuation information is transmission control information instructing transmission of a blood pressure fluctuation notification email, and the fluctuation information output unit 1033 outputs the transmission control information to the communication unit 108. Based on the transmission control information, the communication unit 108 transmits the blood pressure fluctuation notification email to a destination registered in advance. For example, by registering a destination corresponding to the mobile terminal 80 in advance, the communication unit 108 transmits the blood pressure fluctuation notification email to the mobile terminal 80. The mobile terminal 80 receives the blood pressure fluctuation notification email and displays the blood pressure fluctuation notification email. The blood pressure fluctuation information is also notification control information for reporting the blood pressure fluctuation, and the fluctuation information output unit 1033 outputs the notification control information to the display unit 101. The display unit 101 displays a blood pressure fluctuation guide based on the notification control information. For example, the blood pressure fluctuation notification email and the blood pressure fluctuation guide are information visually indicating the blood pressure fluctuation with characters, images, or characters and images. In the case where the blood pressure monitor 1 has a vibration notification function, the blood pressure fluctuation may be reported by vibration of the vibration notification function based on the blood pressure fluctuation information. Furthermore, in the case where the blood pressure monitor 1 includes a speaker, the blood pressure fluctuation may be reported by a sound or a sound effect from the speaker based on the blood pressure fluctuation information.

The configuration of the situation detector 1034 will be described.

The situation detector 1034 detects the current situation of the measurement subject at the time of measuring the blood pressure information by combining at least one of the position information, the acceleration information, the temperature and humidity information, the atmospheric pressure information, the action schedule information, or the like with the time information, and outputs information indicating the current situation. The "detection" may be read as "estimation". The blood pressure information output unit 1037 uses the current situation output from the situation detector 1034 as the blood pressure measurement situation corresponding to the blood pressure measurement.

For example, the situation detector 1034 outputs the environmental information associated with the time information as one of the current situations based on the sequentially acquired environmental information. Accordingly, first environmental information associated with a first environment measurement date and time (hereinafter, also referred to as "current environmental information") and second environmental information associated with a second environment measurement date and time that is earlier than the first environment measurement date and time (hereinafter, also referred to as "past environmental information") are output.

For example, the situation detector 1034 detects whether or not the current position corresponds to a registered position based on the acquired position information (current position) and the pre-registered position information (registered position). For example, in the case where the current position is included in a predetermined range from the registered position, the current position is detected as corresponding to the registered position. That is, the situation detector 1034 can detect whether or not the current position corresponds to the registered position as the current situation. For example, by pre-registering at least one location among a workplace, a home, a hospital, and the like, it is possible to detect whether the current position corresponds to at least one of these locations.

The situation detector 1034 also detects whether or not the current situation corresponds to various situations estimated from the acceleration information based on the acquired acceleration information. For example, the situation detector 1034 can estimate the amount of activity from the acceleration information, and detect whether or not the current situation corresponds to before sleeping, sleeping, or after waking, etc. based on the amount of activity. Furthermore, the situation detector 1034 can detect whether or not the current situation is during exercising and whether or not the current situation is after exercising based on the activity amount information.

Furthermore, the situation detector 1034 detects whether or not the current situation corresponds to the situation of the action schedule information based on the acquired time information (current time) and the acquired action schedule information. For example, the situation detector 1034 can detect which situation the current situation corresponds to, such as before sleeping, during sleeping, or after waking, by using the current time and the action schedule information instead of the acceleration information. For example, the situation detector 1034 detects that the current situation corresponds to sleeping based on the current time 23:00 and the action schedule information including the scheduled sleeping time 22:00 and the scheduled awakening time 7:00.

The configuration of the environmental change detector 1035 will be described.

The environmental change detector 1035 holds the first environmental information (current environmental information) and the second environmental information (past environmental information) based on environmental information sequentially acquired over time, and sequentially updates the first and second environmental information based on the environmental information sequentially acquired over time. For example, at a first timing, the environmental information acquired at the first timing becomes the first environmental information, at a second timing after the first timing, the environmental information acquired at the second timing becomes the new first environmental information, and at the second timing, the first environmental information acquired at the first timing becomes the second environmental information. The environmental change detector 1035 detects an environmental change exceeding an environmental reference value (second reference value) from the updated first environmental information and the updated second environmental information, and outputs a trigger signal for starting blood pressure measurement based on the detection of the environmental change. For example, in the case where a difference between the first environmental information of the first environment measurement date and time obtained by a measurement and the second environmental information obtained by a past measurement of the second environment measurement date and time older than the first measurement date and time exceeds the environment reference value, the difference is detected as the environmental change. The second environment measurement date and time and the second blood pressure measurement date and time may be substantially the same associated date and time or may be independent dates and times. Alternatively, in the case where a difference between the first environmental information of the first environment measurement date and time obtained by a measurement and the average value of a plurality of pieces of second environmental information obtained by a plurality of measurements performed earlier than the first environment measurement date and time exceeds the environment reference value, the difference is detected as the environmental change. For example, in the case where a difference between the first environmental information and an average value of a plurality of pieces of environmental information in the past hour, the past six hours, the past day, or the past week exceeds an environmental reference value, the difference is detected as the environmental change. Note that an environment measurement date and time among a plurality of environment measurement dates and times may be substantially the same date and time associated with the second blood pressure measurement date and time described above, or the plurality of environment measurement dates and times and the second blood pressure measurement date and time may be independent dates and times. For example, a temperature change exceeding a first temperature reference value (second reference value) is detected from current temperature information, which is one of the pieces of first environmental information, and past temperature information, which is one of the pieces of second environmental information. For example, the first temperature reference value is set to 5° C. Furthermore, the environmental change detector 1035 may be configured to detect the temperature change in the case where at least one of the current or the past temperature information is below a second temperature reference value. For example, the second temperature reference value is set to 15° C. Thus, a temperature change at a relatively low temperature is detected.

Furthermore, a change in temperature (room temperature) from the previous night to the next morning may be detected by setting current and past conditions. For example, the environmental change detector 1035 detects, from the current temperature information (temperature information included in the morning time zone from 4:00 a.m. to 6:00 a.m. on the current day) and the past temperature information (temperature information included in the night time zone from 9:00 p.m. to 11:00 p.m. on the previous day), a temperature change from the previous night to the next morning exceeding the first temperature reference value. Furthermore, by setting the first temperature reference value to a relatively high value, a sharp temperature change can be detected. For example, by setting the current and past conditions and the first temperature reference value to 5° C. or higher, the environmental change detector 1035 detects a sharp temperature change from the previous night to the next morning. Furthermore, by adding a condition that both the current and past temperature information be below the second temperature reference value to the conditions, a temperature change under a low temperature (for example, winter) condition can be detected. For example, by setting the current and past conditions above, setting the first temperature reference value to 5° C., and setting the second temperature reference value to 10° C., the environmental change detector 1035 detects a sharp temperature change from the previous night to the next morning in winter (less than 10° C.). The environmental change detector 1035 outputs a trigger signal for starting blood pressure measurement based on the detection of these temperature changes.

Furthermore, the environmental change detector 1035 may be configured to detect an atmospheric pressure change exceeding an atmospheric pressure reference value (second reference value) from current atmospheric pressure information, which is one of the pieces of current environmental information, and past atmospheric pressure information, which is one of the pieces of past environmental information.

The configuration of the blood pressure measurement unit 1036 will be described.

For example, the blood pressure measurement unit 1036 controls various operations and measures the blood pressure value of the measurement subject in the following manner based on detection of a measurement instruction output in response to the measurement subject pressing the measurement switch of the operation unit 102 (input operation of blood pressure measurement) or detection of a measurement instruction serving as a trigger for starting blood pressure measurement. The measurement of the blood pressure value by the blood pressure measurement unit 1036 is to calculate the blood pressure value from the sensed data.

For example, the blood pressure measurement unit 1036 initializes the processing memory area of the storage unit 104 based on detection of a measurement instruction or detection of a measurement instruction that triggers the blood pressure measurement to be started. The blood pressure measurement unit 1036 turns off the pump 114 via the pump drive circuit 113, opens the exhaust valve built in the pump 114, maintains the open/close valve 115 in an open state, and performs control so as to exhaust air in the pressing cuff 302 and the sensing cuff 304. The blood pressure measurement unit 1036 controls the first pressure sensor 111 and the second pressure sensor 112 to adjust the pressure to 0 mmHg. The blood pressure measurement unit 1036 turns on the pump 114 via the pump drive circuit 113, maintains the open/close valve 115 in an open state, and performs control to start pressurization of the pressing cuff 302 and the sensing cuff 304. The blood pressure measurement unit 1036 controls the pump 114 to be driven via the pump drive circuit 113 while monitoring the pressures of the pressing cuff 302 and the sensing cuff 304 with the first pressure sensor 111 and the second pressure sensor 112, respectively. The blood pressure measurement unit 1036 performs control so as to send air respectively to the pressing cuff 302 through the first flow path and to the sensing cuff 304 through the second flow path.

The blood pressure measurement unit 1036 waits until the pressure of the sensing cuff 304 reaches a predetermined pressure (for example, 15 mmHg) or until a predetermined time (for example, three seconds) elapses for the driving time of the pump 114. The blood pressure measurement unit 1036 closes the open/close valve 115 and continues the control of supplying air from the pump 114 to the pressing cuff 302 through the first flow path. As a result, the pressing cuff 302 is gradually pressurized to gradually compress the left wrist 90. The back plate 303 transmits the pressing force from the pressing cuff 302 to the sensing cuff 304. The sensing cuff 304 compresses the left wrist 90 (including an artery passing portion 90a).

In this pressurization process, the blood pressure measurement unit 1036 monitors pressure Pc of the sensing cuff 304, that is, the pressure of the artery passing portion 90a of the left wrist 90, by the second pressure sensor 112 in order to calculate a blood pressure value (systolic blood pressure (SBP), diastolic blood pressure (DBP), or the like), and acquires a pulse wave signal Pm as a fluctuation component. The blood pressure measurement unit 1036 calculates a blood pressure value by applying a known algorithm by an oscillometric method based on the pulse wave signal Pm. When the blood pressure value is calculated, the blood pressure measurement unit 1036 performs control to stop the pump 114, open the open/close valve 115, and discharge the air in the pressing cuff 302 and the sensing cuff 304. The blood pressure measurement unit 1036 can calculate the blood pressure value by the above-described control, and outputs the calculated blood pressure value to the blood pressure information output unit 1037 as blood pressure information.

The configuration of the blood pressure information output unit 1037 will be described.

The blood pressure information output unit 1037 receives the current situation output from the situation detector 1034 as the blood pressure measurement situation in accordance with the timing of the blood pressure measurement by the blood pressure measurement unit 1036, and outputs the blood pressure information output from the blood pressure measurement unit 1036 and the blood pressure measurement situation in association with each other. That is, the blood pressure information output unit 1037 outputs the blood pressure-related information including the blood pressure information and the blood pressure measurement situation associated with the blood pressure information to the display unit 101 and the storage unit 104. The display unit 101 displays the blood pressure-related information, and the storage unit 104 stores the blood pressure-related information. By repeating the blood pressure measurement by the blood pressure measurement unit 1036, a plurality of pieces of blood pressure-related information are stored (accumulated) in the storage unit 104. The plurality of pieces of blood pressure-related information include current blood pressure-related information and past blood pressure-related information (a plurality of pieces of past blood pressure-related information corresponding to a plurality of measurements). As described above, the first and second blood pressure information are sequentially acquired and updated based on at least one of the input operation of the blood pressure measurement or the blood pressure measurement schedule.

(Operation)

Blood pressure measurement processing performed based on the intention of the measurement subject will be described.

For example, when the measurement subject presses the measurement switch of the operation unit 102 (input operation of blood pressure measurement), the blood pressure monitor 1 measures blood pressure based on a measurement instruction generated in response to the pressed measurement switch. That is, the blood pressure measurement unit 1036 controls an operation for blood pressure measurement based on a measurement instruction generated in response to the pressed measurement switch of the operation unit 102, and measures blood pressure information such as a blood pressure value. The blood pressure measurement based on such measurement switch operation, etc. in the operation unit 102 is also referred to as manual measurement.

Furthermore, when the blood pressure measurement schedule is registered in the storage unit 104, the information acquisition unit 1031 acquires the blood pressure measurement schedule, and the situation detector 1034 generates a blood pressure measurement instruction based on the blood pressure measurement schedule. For example, the blood pressure measurement schedule includes information of a blood pressure measurement date and time (every six hours (for example, 6:00, 12:00, 18:00, and 0:00) or every day (for example, every morning at 6:00)). The situation detector 1034 generates a blood pressure measurement instruction based on the blood pressure measurement date and time and the current date and time included in the blood pressure measurement schedule. The blood pressure measurement unit 1036 controls an operation for blood pressure measurement based on the blood pressure measurement instruction and measures the blood pressure information. Blood pressure measurement based on such a blood pressure measurement schedule is referred to as schedule measurement. In this embodiment, it is assumed that at least one of the manual measurement or the schedule measurement is performed.

The blood pressure information output unit 1037 receives the current situation output from the situation detector 1034 as the blood pressure measurement situation (including the blood pressure measurement date and time), and outputs the blood pressure information output from the blood pressure measurement unit 1036 and the blood pressure-related information including the blood pressure measurement situation associated with the blood pressure information. The blood pressure information output unit 1037 outputs the blood pressure-related information to the display unit 101 and the storage unit 104. The display unit 101 displays the blood pressure-related information, and the storage unit 104 stores the blood pressure-related information. For example, by repeating the blood pressure measurement, the storage unit 104 stores (accumulates) the blood pressure-related information. Note that at the beginning of measurement, the blood pressure-related information stored in the storage unit 104 is the current blood pressure-related information; however, over time, the blood pressure-related information stored in the storage unit 104 becomes the past blood pressure-related information. That is, the blood pressure-related information is sequentially acquired according to the elapsing of time. As a result, the first and second blood pressure information are sequentially updated.

Blood pressure measurement processing based on an environmental change will now be described.

Figure 5:
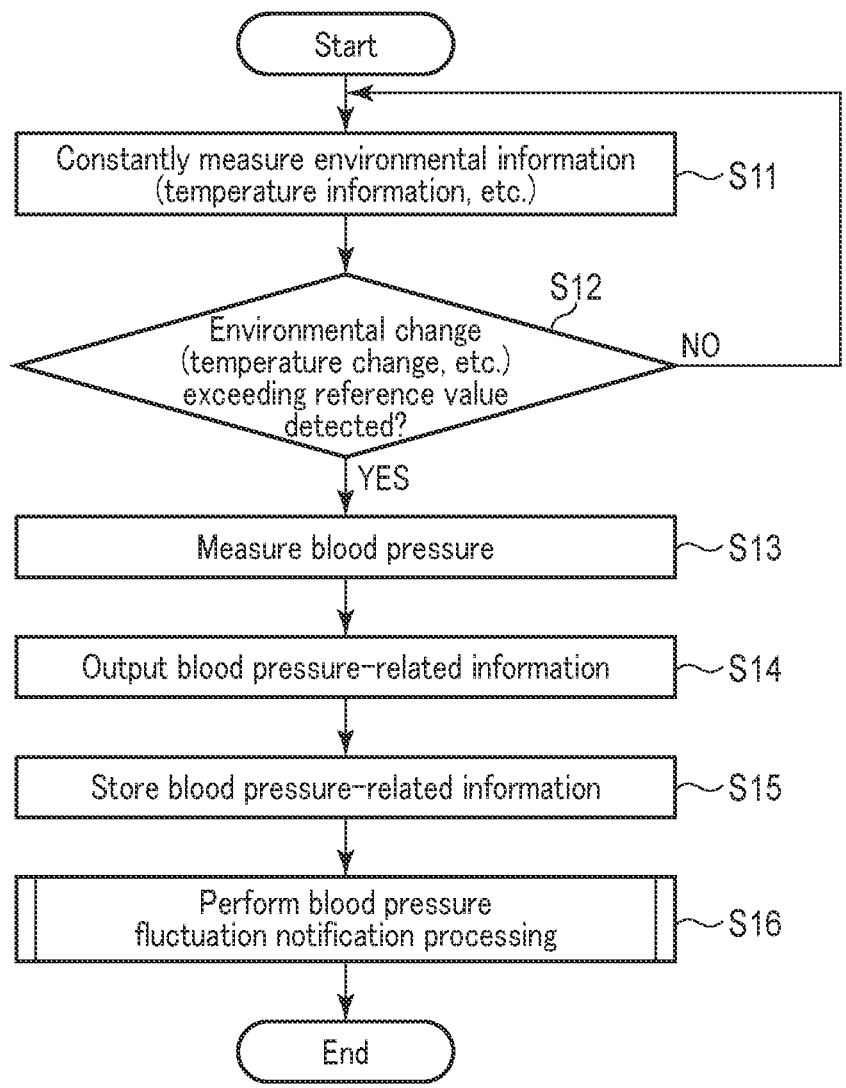
FIG. 5 is a flowchart showing an example of blood pressure measurement processing based on an environmental change according to an embodiment.

FIG. 5 is a flowchart showing an example of the blood pressure measurement processing based on an environmental change according to the embodiment.

As shown in FIG. 5, the blood pressure monitor 1 constantly measures the environmental information (step S11). For example, the temperature and humidity sensor 106 constantly measures temperature and humidity information (step S11). The information acquisition unit 1031 sequentially acquires the time information and the environmental information, and the situation detector 1034 outputs the environmental information in association with the time information. The environmental change detector 1035 detects an environmental change exceeding the reference value from the current and past environmental information (YES in step S12), and outputs a trigger signal for starting blood pressure measurement based on the detection of the environmental change. For example, the environmental change detector 1035 detects a temperature change exceeding the reference value from the current and past temperature information (YES in step S12), and outputs a trigger signal for starting blood pressure measurement based on the detection of the temperature change. If the environmental change detector 1035 does not detect an environmental change exceeding the reference value from the current and past environmental information (NO in step S12), the environmental change detector 120 does not output a trigger signal for starting blood pressure measurement.

The blood pressure monitor 1 measures the blood pressure based on the trigger signal for starting the blood pressure measurement (step S13). That is, the blood pressure measurement unit 1036 controls an operation for blood pressure measurement based on the detection of the environmental change, and measures blood pressure information such as a blood pressure value (step S13). The blood pressure information output unit 1037 outputs the blood pressure-related information including the blood pressure information and the blood pressure measurement situation associated with the blood pressure information (step S14). For example, the blood pressure information output unit 1037 outputs the blood pressure-related information to the display unit 101 and the storage unit 104. The display unit 101 displays the blood pressure-related information, and the storage unit 104 stores the blood pressure-related information (step S15). Note that at the beginning of measurement, the blood pressure-related information stored in the storage unit 104 is the current blood pressure-related information; however, over time, the blood pressure-related information stored in the storage unit 104 becomes the past blood pressure-related information.

The fluctuation information output unit 1033 executes blood pressure fluctuation notification processing based on the detection of blood pressure fluctuation (step S16).

Figure 6:
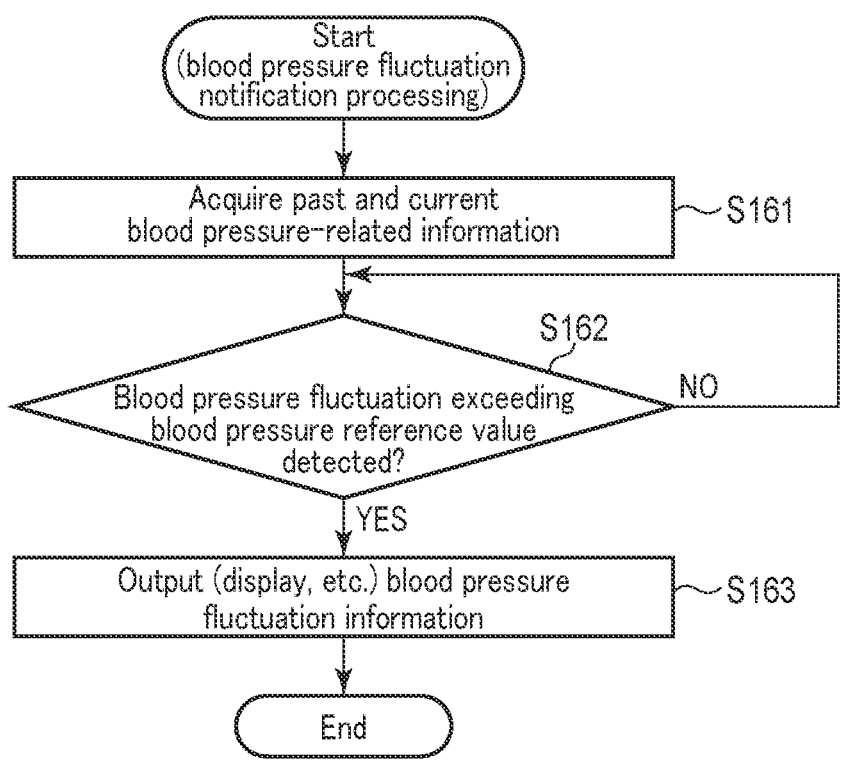
FIG. 6 is a flowchart showing an example of blood pressure fluctuation notification processing according to an embodiment.

FIG. 6 is a flowchart showing the blood pressure fluctuation notification processing according to the embodiment.

As illustrated in FIG. 6, the information acquisition unit 1031 acquires the current and past blood pressure-related information stored in the storage unit 104 (step S161). When the blood pressure fluctuation detector 1032 detects a blood pressure fluctuation exceeding the blood pressure reference value from the current and past blood pressure-related information (YES in step S162), the fluctuation information output unit 1033 outputs the blood pressure fluctuation information for reporting the blood pressure fluctuation based on the detection of the blood pressure fluctuation (step S163). If the blood pressure fluctuation detector 1032 does not detect a blood pressure fluctuation exceeding the blood pressure reference value from the current and past blood pressure-related information (NO in step S162), the blood pressure fluctuation detector 1032 continues to detect the blood pressure fluctuation based on the blood pressure reference value.

For example, the fluctuation information output unit 1033 outputs transmission control information for instructing the communication unit 108 to transmit a blood pressure fluctuation notification email. Based on the transmission control information, the communication unit 108 transmits the blood pressure fluctuation notification email to a destination registered in advance. The fluctuation information output unit 1033 outputs the notification control information to the display unit 101. The display unit 101 displays the blood pressure fluctuation guide based on the notification control information.

Although the case has been described where the storage unit 104 stores the blood pressure-related information and the information acquisition unit 1031 acquires the blood pressure-related information stored in the storage unit 104, the blood pressure-related information may be stored in the memory of the server 70 or the mobile terminal 80 instead of the storage unit 104 of the blood pressure monitor 1, and the information acquisition unit 1031 may acquire the blood pressure-related information stored in the memory of the server 70 or the mobile terminal 80.

Furthermore, the measurement date and time of the past environmental information in step S12 and the measurement date and time of the past blood pressure-related information in step S161 may be substantially the same related date and time, or may be dates and times independent of each other.

(Effect)

As described above in detail, in the embodiment of the present invention, by outputting the blood pressure fluctuation information based on the detection of the blood pressure fluctuation, it is possible to notify the measurement subject and the like of the blood pressure fluctuation by providing an opportunity to recognize the blood pressure fluctuation. For example, a blood pressure fluctuation exceeding the first reference value imposes a burden on the blood vessel; however, since the measurement subject or the like can become aware that a blood pressure fluctuation occurred at the first blood pressure measurement date and time, the measurement subject can discuss improving the living environment or the like at the first blood pressure measurement date and time. For example, the blood pressure fluctuation can be reported immediately after the blood pressure is measured at the first blood pressure measurement date and time. Thus, the measurement subject or the like can become aware that a blood pressure fluctuation occurred under those circumstances at that time. Furthermore, in a case where the blood pressure fluctuation is reported by email or the like, the notification destination may be the email address of the measurement subject or the email address of a related party. For example, an email address of a hospital or a relative may be used. In this way, it is possible to notify the measurement subject himself or herself, and the related party as well.

Furthermore, the blood pressure fluctuation may occur based on a temperature change exceeding the second reference value, and the detection probability of the blood pressure fluctuation can be increased. For example, since a blood pressure fluctuation may occur based on a temperature change, the blood pressure fluctuation can be detected with a relatively high probability by detecting the blood pressure fluctuation based on the temperature change. It should be noted that blood pressure fluctuation can be efficiently detected by adding temperature change detection at a low temperature to the conditions. For example, in a case where at least one of the current temperature information or the past temperature information is below the temperature reference value, an environmental change is detected. Furthermore, since the blood pressure fluctuation may occur based on the atmospheric pressure change, the blood pressure fluctuation can be detected with a relatively high probability by detecting the blood pressure fluctuation based on the atmospheric pressure change.

Furthermore, by adding various kinds of information to the blood pressure fluctuation information for reporting the blood pressure fluctuation, it is possible to notify the measurement subject or the like of various kinds of information together with the blood pressure fluctuation. For example, by adding at least one of the information indicating the environmental change or the information indicating the blood pressure measurement situation to the blood pressure fluctuation information, it is possible to notify the measurement subject or the like of at least one of the environmental change or the blood pressure measurement situation together with the blood pressure fluctuation. For example, the fluctuation value of the blood pressure and the fluctuation value of the temperature can be reported to the measurement subject or the like. Furthermore, by including a blood pressure measurement position such as a home or a workplace in the blood pressure measurement situation, the blood pressure measurement position can be reported to the measurement subject or the like.

Furthermore, if the measurement date and time of the past environmental information and the measurement date and time of the past blood pressure-related information are substantially the same date and time, it is possible to detect and report a blood pressure fluctuation directly affected by an environmental change. Furthermore, if the measurement date and time of the past environmental information and the measurement date and time of the past blood pressure-related information are independent dates and times, it is possible to detect and report a blood pressure fluctuation indirectly affected by an environmental change.

Other Embodiments

Although the case where the blood pressure fluctuation is detected in the blood pressure monitor 1 has been described, the embodiment is not limited thereto. The server 70 or the mobile terminal 80 may detect the blood pressure fluctuation and notify the blood pressure monitor 1 of the blood pressure fluctuation detection result. For example, the server 70 or the mobile terminal 80 receives and stores the current and past blood pressure-related information from the blood pressure monitor 1. The server 70 or the mobile terminal 80 detects the blood pressure fluctuation from the current and past blood pressure-related information, and notifies the blood pressure monitor 1 of the blood pressure fluctuation detection result. The blood pressure monitor 1 receives the blood pressure fluctuation detection result from the server 70 or the mobile terminal 80, and outputs blood pressure fluctuation information for reporting the blood pressure fluctuation based on the blood pressure fluctuation detection result. Alternatively, the server 70 or the mobile terminal 80 may output the blood pressure fluctuation information for reporting the blood pressure fluctuation based on the blood pressure fluctuation detection result. The communication unit 108 of the blood pressure monitor 1 receives the blood pressure fluctuation information from the server 70 or the mobile terminal 80, and the display unit 101 or the like reports the blood pressure fluctuation based on the blood pressure fluctuation information.

As described above, the blood pressure monitor 1 is not limited to a blood pressure monitor (non-continuous blood pressure monitor) that starts blood pressure measurement based on detection of an input of a blood pressure measurement instruction or detection of a trigger signal autonomously generated by the blood pressure monitor 1. For example, the blood pressure monitor 1 may be a blood pressure monitor (continuous blood pressure monitor) employing a continuous measurement-type blood pressure detection method using a pulse transmit time (PTT) method, a tonometry method, an optical method, a radio wave method, an ultrasonic method, or the like. For example, a continuous blood pressure monitor executes the blood pressure fluctuation notification processing shown in FIG. 6. The PTT method is a method of measuring a pulse transit time (PTT) and estimating a blood pressure value from the measured pulse transit time. The tonometry method is a method in which a pressure sensor is brought into direct contact with a biological site (measurement site) through which an artery passes, such as a radial artery of a wrist, and a blood pressure value is measured using information detected by the pressure sensor. The optical method, the radio wave method, and the ultrasonic method are methods in which light, radio waves, or ultrasonic waves are applied to a blood vessel, and a blood pressure value is measured from reflected waves thereof.

Furthermore, the continuous blood pressure monitor may transmit the current and past blood pressure-related information to the server 70 or the mobile terminal 80, and the server 70 or the mobile terminal 80 may detect the blood pressure fluctuation from the current and past blood pressure-related information and notify the continuous blood pressure monitor of the blood pressure fluctuation detection result.

Furthermore, in the above-described embodiment, the case of measuring blood pressure has been described as an example. However, the present invention is not limited thereto, and the present invention can also be applied to the case of measuring other biological information such as an activity amount, the number of steps, an electrocardiogram, a pulse rate, and a body temperature.

The various functional units described in the above embodiments may be realized by using circuits. The circuit may be a dedicated circuit that implements a specific function or may be a general-purpose circuit such as a processor.

At least a part of the processing of each of the above embodiments can also be realized by using a general-purpose computer as basic hardware. The program for realizing the above-described processing may be provided by being stored in a computer-readable recording medium. The program is stored in a recording medium as a file in an installable format or a file in an executable format.

Examples of the recording medium include a magnetic disk, an optical disc (such as a compact disc-read only memory (CD-ROM), a compact disc-recordable (CD-R), and a digital versatile disc (DVD)), a magneto-optical disc (such as a magneto optical (MO)), and a semiconductor memory. The recording medium may be any medium as long as it can store the program and can be read by a computer. Furthermore, the program for realizing the above-described processing may be stored in a computer (server) connected to a network such as the Internet and downloaded to a computer (client) via the network.

A part or all of the above-mentioned embodiments may also be described as in the following supplementary notes, without limitation thereto.

(Supplementary note 1)

An information processing apparatus comprising:

a processor configured to acquire first blood pressure information associated with a first blood pressure measurement date and time and second blood pressure information associated with a second blood pressure measurement date and time that is earlier than the first blood pressure measurement date and time, detect a blood pressure fluctuation exceeding a first reference value from the first and second blood pressure information, and output blood pressure fluctuation information reporting the blood pressure fluctuation; and a memory configured to store a command to cause the processor to operate.

(Supplementary note 2)

An information processing method comprising:

acquiring, by using at least one processor, first blood pressure information associated with a first blood pressure measurement date and time and second blood pressure information associated with a second blood pressure measurement date and time that is earlier than the first blood pressure measurement date and time;

detecting, by using the at least one processor, a blood pressure fluctuation exceeding a first reference value from the first and second blood pressure information; and outputting, by using the at least one processor, blood pressure fluctuation information reporting the blood pressure fluctuation.

REFERENCE SIGNS LIST

1 . . . blood pressure monitor
10 . . . main body
10A . . . case
10B . . . glass
10C . . . back cover
20 . . . belt
30 . . . cuff structure
30a . . . one end
30b . . . other end
30c . . . inner peripheral surface
70 . . . server
80 . . . mobile terminal
90 . . . left wrist
90a . . . artery passing portion
91 . . . radial artery
92 . . . ulnar artery
93 . . . radius
94 . . . ulna
95 . . . tendon
101 . . . display unit
102 . . . operation unit
103 . . . controller
104 . . . storage unit
105 . . . acceleration sensor
106 . . . temperature and humidity sensor
107 . . . atmospheric pressure sensor
108 . . . communication unit
109 . . . GPS receiver
110 . . . battery
111 . . . first pressure sensor
112 . . . second pressure sensor
113 . . . pump drive circuit
114 . . . pump
115 . . . open/close valve
201 . . . first belt portion
201a . . . root portion
201b . . . distal end portion
202 . . . second belt portion
202a . . . root portion
202b . . . distal end portion
202c . . . small hole
203 . . . buckle
203A . . . frame-like body
203B . . . fastening rod
203C . . . connecting rod
204 . . . belt holding portion
301 . . . curler
302 . . . pressing cuff
303 . . . back plate
304 . . . sensing cuff
304A . . . first sheet
304B . . . second sheet
401 . . . connecting rod
402 . . . connecting rod
501 . . . flexible tube
502 . . . flexible tube
503 . . . first flow path forming member
504 . . . second flow path forming member
1031 . . . information acquisition unit
1032 . . . blood pressure fluctuation detector
1033 . . . fluctuation information output unit
1034 . . . situation detector
1035 . . . environmental change detector
1036 . . . blood pressure measurement unit
1037 . . . blood pressure information output unit

The invention claimed is:

1. An information processing apparatus comprising:
an environmental change detector configured to detect an environmental change exceeding a first reference value from first environmental information and second environmental information that is information earlier than the first environmental information;
a blood pressure measurement unit configured to measure first blood pressure information based on detection of the environmental change;
a blood pressure information output unit configured to output the first blood pressure information;
an information acquisition unit configured to acquire first blood pressure information and second blood pressure information that is information earlier than the first blood pressure information;
a blood pressure fluctuation detector configured to detect a blood pressure fluctuation exceeding a second reference value from the first and second blood pressure information; and
a fluctuation information output unit configured to output blood pressure fluctuation information that reports the blood pressure fluctuation, wherein
the environmental change detector detects the environmental change in a case where at least one of first temperature information corresponding to the first environmental information or second temperature information corresponding to the second environmental information is below a temperature reference value.

2. The information processing apparatus according to claim 1, wherein
the blood pressure measurement unit measures the second blood pressure information based on one of a measurement instruction corresponding to an input operation or a measurement instruction corresponding to a measurement schedule, and
the blood pressure information output unit outputs the second blood pressure information.

3. The information processing apparatus according to claim 2, wherein the blood pressure fluctuation detector updates the second blood pressure information in accordance with acquisition of blood pressure information.

4. The information processing apparatus according to claim 1, wherein the environmental change detector updates the second environmental information in accordance with acquisition of environmental information.

5. The information processing apparatus according to claim 1, wherein the fluctuation information output unit outputs the blood pressure fluctuation information including information indicating the environmental change.

6. The information processing apparatus according to claim 1, wherein
the blood pressure information output unit outputs the first and second blood pressure information in association with information indicating a blood pressure measurement situation of a measurement subject, and
the fluctuation information output unit outputs the blood pressure fluctuation information including information indicating the blood pressure measurement situation.

7. The information processing apparatus according to claim 6, wherein the information indicating the blood pressure measurement situation includes a blood pressure measurement position of the measurement subject.

8. An information processing method performed by an information processing apparatus, the information processing method comprising:
- detecting an environmental change exceeding a first reference value from first environmental information and second environmental information that is information earlier than the first environmental information;
- measuring first blood pressure information based on detection of the environmental change;
- outputting the first blood pressure information;
- acquiring first blood pressure information and second blood pressure information that is information earlier than the first blood pressure information;
- detecting a blood pressure fluctuation exceeding a second reference value from the first and second blood pressure information; and
- outputting blood pressure fluctuation information reporting the blood pressure fluctuation, wherein
- the detecting the environmental change is performed in a case where at least one of first temperature information corresponding to the first environmental information or second temperature information corresponding to the second environmental information is below a temperature reference value.

9. A non-transitory computer-readable storage medium storing an information processing program that causes a computer to function as each unit included in the information processing apparatus according to claim 1.

* * * * *